United States Patent
Körber et al.

(10) Patent No.: US 6,693,069 B2
(45) Date of Patent: Feb. 17, 2004

(54) DISINFECTING COMPOSITIONS AND PROCESSES FOR DISINFECTING SURFACES

(75) Inventors: Heinz-Otto Körber, Wuppertal (DE); Thomas Merz, Hilden (DE); Christian Roth, Bornheim (DE); Bernhard Meyer, Mettmann (DE)

(73) Assignee: Ecolab GmbH & Co. oHG, Dusseldorf (DE)

( * ) Notice: Subject to any disclaimer, the term of this patent is extended or adjusted under 35 U.S.C. 154(b) by 41 days.

(21) Appl. No.: 10/168,426

(22) PCT Filed: Dec. 14, 2000

(86) PCT No.: PCT/EP00/12695

§ 371 (c)(1), (2), (4) Date: Jun. 21, 2002

(87) PCT Pub. No.: WO01/48136

PCT Pub. Date: Jul. 5, 2001

(65) Prior Publication Data

US 2003/0045443 A1 Mar. 6, 2003

(30) Foreign Application Priority Data

Dec. 23, 1999 (DE) .......................................... 199 62 343

(51) Int. Cl.⁷ ............................. C11D 1/04; C11D 3/00; D06L 1/04

(52) U.S. Cl. ........................................ 510/310; 510/292

(58) Field of Search ................................. 510/292, 302, 510/303, 310, 316, 353

(56) References Cited

U.S. PATENT DOCUMENTS 5,489,434 A  2/1996  Oakes et al.

FOREIGN PATENT DOCUMENTS

| DE | 31 12 242 | 1/1983 |
| DE | 31 21 242 | 1/1983 |
| DE | 40 12 769 | 10/1991 |
| DE | 42 28 786 | 3/1994 |
| EP | 0 442 549 | * 8/1991 |
| EP | 0 610 010 | 8/1994 |
| WO | WO 91/03590 | 3/1991 |
| WO | WO 98/54279 | 12/1998 |
| WO | WO 00/15750 | 3/2000 |

* cited by examiner

Primary Examiner—Yogendra N. Gupta
Assistant Examiner—John M Petruncio
(74) Attorney, Agent, or Firm—Merchant & Gould P.C.

(57) ABSTRACT

The invention relates to methods and agents for washing textiles while disinfecting them and treating the same with care, whereby a combination consisting of peracid and particular additional constituents is used as the disinfection constituent.

21 Claims, No Drawings

DISINFECTING COMPOSITIONS AND PROCESSES FOR DISINFECTING SURFACES

The present invention relates to the use of peracid-containing combinations for the disinfecting washing of textiles and to special peracid-containing textile and wool disinfectants and to processes for the gentle disinfecting washing of textiles.

It is known from the prior art that peracid compounds can be used in the washing of textiles. The peracid compounds normally used can have a disinfecting effect, depending on the particular type of peracid compound and the temperature and concentration used in the washing process.

It is also known from the prior art that textiles or textile fibers are permanently damaged in the washing process if peracids, for example peracetic acid, are used. This applies particularly to the washing of delicate textiles consisting of materials such as wool, silk, polyacrylics, viscose, polyamide, acetate and lyocell.

The extent of the damage is additionally influenced by the conditions of the washing process such as mechanics, temperature, time, concentration and type of chemistry.

Textiles are damaged to a greater or lesser extent, depending on the conditions. In the case of woolen textiles, vigorous mechanical action causes the textile fibers to hook together irreversibly, causing wool to shrink considerably. The washing conditions also determine whether and to what extent the polymer structure of the textiles is changed. A change to the polymer structure reduces the tensile strength of textiles. In the case of wool, this results in increased alkali solubility.

To solve this problem, the disinfecting washing process has to be carried out under particularly gentle conditions.

It is known from the prior art that the fiber-damaging effect can be reduced by lowering the temperature. Furthermore, a light-duty detergent which is less harmful to the textile fibers is generally used for the washing of delicate textiles.

Nevertheless the addition of sufficiently effective amounts of peracid compounds, even when combined with conventional light-duty detergents, leads to the above-described drawbacks in the disinfecting washing process, even at low washing temperatures, such as 30° C. to 40° C.

For this reason, other active ingredients for the disinfecting washing of textiles have been investigated in the prior art.

It has been found that disinfectants based on quaternary ammonium compounds do not generally have an adequate disinfecting effect during disinfecting washing at low temperatures. Pronounced damage to textiles is observed during experiments using disinfectants based on aldehydes.

Accordingly, the problem addressed by the present invention was to enable textiles and particularly delicate textiles to be subjected to disinfecting washing at low temperatures with minimal damage to the textiles or textile fibers.

The present invention relates to the use of a disinfecting component containing a combination of peracid and
  a) at least one fatty acid and/or
  b) at least one hydrotrope and/or
  c) at least one surfactant component and/or
  d) at least one complexing component for the disinfecting washing of textiles.

The effect of using disinfecting components of this type is preferably that the degree of fiber damage in the disinfecting washing of textiles is less than it is where the corresponding peracids alone are used in the same quantities, even if they are added to the washing solution together with perborate-containing, fully-built or light-duty detergents which already contain fatty acids, hydrotropes or components having surfactant and/or complexing properties.

In a preferred embodiment of the present invention, the disinfecting components to be used according to the invention are used for the gentle disinfecting washing of textiles which are sensitive to oxidative disinfectants and/or heat.

In another preferred embodiment, textiles which are sensitive to oxidative disinfectants and/or heat are subjected to disinfecting washing at a temperature of 10 to 55° C. and more particularly at a temperature of 20 to 45° C.

The textiles which are sensitive to oxidative disinfectants and/or heat preferably contain materials selected from wool, acetate, lyocell, silk, viscose, acrylic fibers and polyamide.

The disinfecting components to be used in accordance with the invention are preferably used together with standard speciality, color, fully-built and light-duty detergents.

The disinfecting component to be used in accordance with the invention preferably contains as peracid a compound selected from
  a) the peracids or salts of peracids corresponding to general formula I $$R^2\text{—}O_2C\text{—}(CH_2)_x\text{—}CO_3H \qquad (I)$$

in which $R^2$ is hydrogen or an alkyl group containing 1 to 4 carbon atoms, more particularly hydrogen and/or methyl, and x is a number of 1 to 4, and/or
  b) phthalimidopercarboxylic acids (II) where the percarboxylic acid contains 1 to 18 carbon atoms and more particularly 1 to 8 carbon atoms, and/or
  c) compounds corresponding to formula III:

$$R^1\text{—}CO_3H \qquad (III)$$

in which $R^1$ is an alkyl or alkenyl group containing 1 to 18 carbon atoms and more particularly 1 to 12 carbon atoms.

In a most particularly preferred embodiment of the present invention, the disinfecting component to be used in accordance with the invention contains one or more compounds selected from peracetic acid, perpropionic acid, peroctanoic acid, phthalimidoperhexanoic acid, phthalimidoperoctanoic acid, persuccinic acid, persuccinic acid monomethyl ester, perglutaric acid, perglutaric acid monomethyl ester, peradipic acid, peradipic acid monomethyl ester, persuccinic acid, persuccinic acid monomethyl ester.

In a preferred embodiment, an aqueous disinfecting washing solution in which the peracid content between 0.0001 and 2% by weight and more particularly between 0.001 and 0.2% by weight, based on the disinfecting washing solution as a whole, is produced by addition of the disinfecting component.

In another preferred embodiment of the present invention, an aqueous disinfecting washing solution additionally containing 0.0005 to 2% by weight and more particularly 0.005 to 0.8% by weight of hydrogen peroxide, based on the disinfecting washing solution as a whole, is produced by addition of the disinfecting component to be used in accordance with the invention.

Preferably, the disinfecting component additionally contains the non-oxidized acid corresponding to the peracid present and, in the case of the peracid esters, also the corresponding non-esterified form of the non-oxidized acid.

A fatty acid containing 8 to 12 carbon atoms, more particularly octanoic acid, is preferably present as the fatty acid in the disinfecting component to be used in accordance with the invention.

The hydrotrope is preferably selected from the group of anionic surfactants, preferably from the sulfonates/sulfonic acids and in particular from cumene, xylene, octyl, napthyl and alkylbenzenesulfonates/sulfonic acids, the alkyl group in the last of these containing between 6 and 16 carbon atoms.

The disinfecting component to be used in accordance with the invention preferably contains as surfactant component a compound selected from the groups consisting of anionic, cationic, nonionic, amphoteric surfactants, protein hydrolyzates, for example Lamepon types, alkylamine oxides, silicone compounds and phosphoric acid esters and salts thereof.

Cationized protein hydrolyzates are most particularly preferred in this connection. These are, for example, partly hydrolyzed collagens which, after modification with epichlorohydrin, are reacted with alkyl dimethylamine to form quaternary ammonium chloride. The alkyl group of the amine preferably contains 8 to 20 carbon atoms Suitable anionic surfactants are any anionic surfactants commonly used in the field of detergents and cleaning agents, for example $C_8$–$C_{18}$ alkyl sulfates, $C_8$–$C_{18}$ alkyl ether sulfates, $C_8$–$C_{18}$ alkanesulfonates, $C_8$–$C_{18}$-α-olefin sulfonates, sulfonated $C_8$–$C_{18}$ fatty acids, $C_8$–$C_{18}$ alkyl benzenesulfonates, sulfosuccinic acid mono- and di-$C_1$–$C_{12}$-alkyl esters, $C_8$–$C_{18}$ alkyl polyglycolether carboxylates, $C_8$–$C_{18}$ N-acyltaurides, $C_8$–$C_{18}$ N-sarcosinates, $C_8$–$C_{18}$ alkylisethionates and mixtures thereof.

The amine oxide is preferably trialkylamine oxide with one alkyl group containing 8 to 20 carbon atoms and two alkyl groups containing a smaller number of carbon atoms in the alkyl chain, the two shorter alkyl groups being the same or different. In a particularly preferred embodiment, the amine oxide derivative is tallow bis-(2-hydroxyethyl)-amine oxide, oleyl bis-(2-hydroxyethyl)-amine oxide, coconut bis-(2-hydroxyethyl)-amine oxide, tetradecyl dimethylamine oxide and/or alkyl dimethylamine oxide containing 12 to 18 carbon atoms in the alkyl chain.

The nonionic surfactants in the disinfecting component to be used in accordance with the invention are preferably alkylpolyglucosides which can normally be obtained on an industrial scale by condensation of fatty alcohols with glucose or polyglucose and which are commercially available in various forms. Examples of alkylpolyglucosides which are particularly suitable for the use claimed in the invention include the products Glucopon® 600 (Henkel) and Triton® BG10 (Rohm & Haas).

Other preferred nonionic surfactants are alkoxylated alkyl alcohols containing 8 to 22 carbon atoms in the alkyl chain. In one particular embodiment, at least one compound from the groups consisting of mixed ethoxylates/propoxylates of branched or unbranched alkyl alcohols containing 8 to 22 carbon atoms in the alkyl chain and end-capped ethoxylates of branched or unbranched alkyl alcohols containing 8 to 22 carbon atoms in the alkyl chain is present. In a most particularly preferred embodiment, at least one compound from the groups consisting of ethoxylated and propoxylated alkyl alcohols containing 12 to 22 carbon atoms in the alkyl moiety, the butyl ethers of ethoxylated alkyl alcohols containing 12 to 22 carbon atoms in the alkyl moiety and methyl ethers of ethoxylated alkyl alcohols containing 12 to 22 carbon atoms in the alkyl moiety is present, butyl ethers and methyl ethers of ethoxylated 2-octyl-1-dodecanol being present in special cases.

Nonionic surfactants which are particularly suitable for producing the formulations according to the invention are, for example, Plurafac® LF 403, Plurafac® 431 (BASF) and Dehypon® LT 104 and Dehypon® G 2084 (Henkel).

Phosphoric acid ester compounds, preferably including at least one salt of a phosphoric acid partial ester, are preferably used as phosphonic acid esters in the disinfecting component to be used in accordance with the invention. In a particularly preferred embodiment, at least one alkali metal salt of a phosphoric acid partial ester of alkoxylated alkyl phenol is present.

Phosphoric acid esters are surface-active substances preferably derived from long-chain aliphatic or araliphatic alcohols. Salts of phosphoric acid partial esters, especially those of alkoxylated alkyl phenols, have proved to be particularly suitable. Sodium and potassium salts are preferably used as the alkali metal salts, the potassium salts being particularly preferred. Surface-active phosphoric acid partial esters of the type preferably used in accordance with the invention are commercially available. One example of an active ingredient of this type which is particularly suitable for the purposes of the invention is the product Triton® H 66 (Rohm & Haas).

The disinfecting component to the used in accordance with the invention preferably contains as the complexing component a compound selected from nitrilotriacetic acid, ethylenediamine tetraacetic acid, methylglycine diacetic acid, gluconic acid, citric acid, dicarboxymethyl-L-glutamic acid, serine diacetic acid, imidosuccinic acid and the group of polycarboxylic and phosphonic acids and their salts.

Examples of polycarboxylic acids are polyacrylic acids and copolymers of maleic anhydride and acrylic acid and the sodium salts of these polymeric acids. Commercially available products include Sokalan® CP 5 and PA 30 (BASF), Alcosperse® 175 and 177 (Alco), LMW® 45 N and SPO2 ND (Norsohaas). Suitable native polymers include oxidized starch (for example DE 42 28 786) and polyamino acids, such as polyglutamic acid or polyaspartic acid, available for example from Cygnus, Bayer, Rohm & Haas, Rhône-Poulenc or SRCHEM.

Examples of phosphonic acids are 1-hydroxyethane-1,1-diphosphonic acid, diethylenetriamine pentamethylene phosphonic acid or ethylenediamine tetramethylene phosphonic acid and alkali metal salts thereof.

The disinfecting component to be used in accordance with the invention is preferably introduced into the disinfecting washing process as an aqueous solution, gel, emulsion, paste, dispersion, powder, granules, flakes, beads, tablets, blocks or extrudates.

In another preferred embodiment, the disinfecting components are diluted with water, if necessary, before or during use in the disinfecting washing process. A particularly preferred dilution factor is between 10 and 10,000.

The disinfecting components to be used in accordance with the invention are preferably used for the disinfecting washing of domestic, hotel, restaurant, hospital, bed, operating theater or military laundry as well as work clothes, dirt absorbing mats, roller towels, mops, special textiles and/or laundry from penal establishments, old people's homes, homes for the handicapped, nursing homes, the laundry preferably including delicate textiles.

The present invention also relates to a textile disinfectant containing peracid in combination with a) at least one hydrotrope and/or
b) at least one fatty acid and/or
c) at least one surfactant component and/or
d) at least one complexing component The foregoing explanations regarding the composition of the disinfecting component to be used in accordance with the invention are also preferred embodiments of the textile disinfectant according to the invention.

The present invention also relates to a wool disinfectant containing peracid in combination with a) at least one fatty acid and/or b) at least one hydrotrope and/or c) at least one surfactant component and/or d) at least one complexing component.

The foregoing explanations regarding the composition of the disinfecting component to be used in accordance with the invention are also preferred embodiments of the wool disinfectant according to the invention.

Both the wool and the textile disinfectant according to the invention preferably contain 1 to 20% by weight of peracid in combination with a) 0.1 to 10% by weight of fatty acid and/or b) 0.1 to 10% by weight of hydrotrope and/or c) 0.1 to 10% by weight of surfactant component and/or d) 0.1 to 10% by weight of complexing component, based on the composition as a whole, as disinfecting components. These quantities also apply to the disinfecting component to be used in accordance with the invention, as explained in the foregoing. In one particularly preferred embodiment, an ester peracid corresponding to formula I is present as peracid in the disinfectant together with more than 35% by weight of hydrogen peroxide, based on the disinfectant as a whole.

By formulating the detergent in this way, the fungicidal effect of the disinfectant can be considerably improved, as can also be seen from the Examples.

The present invention also relates to a washing process for the disinfecting washing of textiles in which a peracid and a) octanoic acid and/or b) octyl sulfonate and/or c) a cationized protein hydrolyzate are contacted with the textiles. In a particularly preferred embodiment, at least one peracid-containing product and a second product which contains components a) and/or c) are used in the process.

EXAMPLES

Example 1

In a first test, the influence of various chemicals on the shrinkage of wool was examined under standardized washing conditions. The result of this test is expressed as the so-called wool shrinkage in percent which indicates the percentage by which a standard woolen textile (IWS Wolftextilien) shrinks during each wash cycle. In a first wash, the standard test textiles (IWS Wolltextilien) were treated for 20 minutes at a temperature of 30° C. In a second wash, corresponding standard test textiles were treated for 20 minutes at 40° C. The corresponding washes were carried out ten times in total and the wool shrinkage then obtained was subsequently divided by 10 in order to obtain the average wool shrinkage for each wash cycle.

A comparison test was carried out with an aqueous disinfecting washing solution containing 0.4% of a commercially available light-duty detergent A and 0.3% of a peracetic acid product A (containing about 0.9% of peracetic acid and about 20% of hydrogen peroxide).

It is known that the peracetic acid in these formulations is mainly responsible for the disinfecting effect at the temperature mentioned. Accordingly, the same quantity of peracetic acid, namely 0.4% of a peracetic product B (containing about 9% of peracetic acid, about 12% of hydrogen peroxide and about 4% of octanoic acid) as in the comparison test was used in the test according to the invention and the same commercially available light-duty detergent A was used in a concentration of 0.4%.

In addition to the influence on the shrinkage of wool, the influence on tensile strength and alkali solubility in washing processes carried out at 30° C. and 40° C. were also investigated. The results are set out in Table 1.

TABLE 1 effect of various disinfecting components on wool shrinkage behavior, tensile strength and alkali solubility

| 20 minutes washing with | Wool shrinkage [%] | Loss of tensile strength (%) after 10 wash cycles | Alkali solubility (%) after 10 wash cycles |
|---|---|---|---|
| Comparison tests: | | | |
| V1 at 30° C.: 0.4% commercial light-duty detergent A and 0.3% peracetic acid product A | 2.7 | 23 | 54 |
| V2 at 40° C.: 0.4% commercial light-duty detergent A and 0.3% peracetic acid product A | 2.9 | 25.2 | 63.8 |
| Tests according to the invention: | | | |
| E1 at 30° C.: 0.4% commercial light-duty detergent A and 0.3% peracetic acid product B | 1.8 | 16.1 | 37 |
| E2 at 40° C.: 0.4% commercial light-duty detergent A and 0.3% peracetic acid product B | 1.8 | 17.3 | 41 |

*including 6% by weight protein hydrolyzate

The conventional commercial light-duty detergent A contains inter alia a combination of alkylbenzenesulfonate, triethanolamine, citrate and nonionic surfactant and alcohols.

It can be seen from Table 1 that different results in regard to wool shrinkage behavior, loss of tensile strength and alkali solubility are obtained in disinfecting washing with peracetic acid, depending on the additives present in the disinfecting component.

This test shows clearly that the octanoic acid influences the result of the disinfecting washing process.

Example 2

The chemothermal laundry disinfecting potential of washing solutions according to Table 1 (see VI, V2) at 40° C. was investigated in a second test where the exposure time was 20 minutes. *Mycobacterium terrae* was used as test germ and the reduction factors for this test germ were investigated. The germ count per germ carrier was greater than $10^6$ both in the test with the disinfecting washing solution of the comparison test (V1, V2) and in the test with the disinfecting washing solution according to the present invention (EI, E2).

The test result shows that reduction factors of greater than 6 are achieved in disinfecting washing at 40° C. both with the comparison washing solution and with the washing solution according to the invention. These results confirm that adequate disinfecting activity in the disinfecting washing process is achieved both with the combination of peracetic acid and light-duty detergents and with the combination of peracetic acid and additional components according to the present invention and light-duty detergents.

Example 3

In a third series of tests, the antimicrobial action spectrum of various combinations of peracids with selected additives was investigated in the DVG Quantitative Suspension Test at ambient temperature.

*Staphylococcus aureus* and *Escherichia coli* were used as test germs for determining bactericidal activity. *Saccharomyces cerevisiae* and *Aspergillus niger* were used as test germs for determining fungicidal activity. The formulations tested are shown in Table 2. Table 3 and Table 4 show the results of the Quantitative Suspension Test.

It can be seen from the tabulated results that the action spectrum of peracids can be significantly improved by selected combinations. This is particularly important because a broad range of ubiquitous microorganisms adheres to textiles.

TABLE 2

Formulations for the microbiological tests

| Raw material | F1 | F2 | F3 | F4 | F5 | F6 | F7 | Comp. F1 | Comp. F2 |
|---|---|---|---|---|---|---|---|---|---|
| Perglutaric acid monomethyl ester mixture (10%) [contains hydrogen peroxide] | 80 | 80 | 80 | 80 | — | 20 | 20 | — | 100 |
| Peracetic acid (10%) [contains hydrogen peroxide] | — | — | — | — | 80 | — | — | 100 | — |
| Alkyl benzenesulfonic acid | 10 | — | — | 10 | 10 | 10 | 10 | — | — |
| Additional hydrogen peroxide | — | — | — | — | — | 42 | 42 | — | — |
| Dimethyl coconut amine oxide | — | 10 | — | — | — | — | — | — | — |
| Sodium octyl sulfonate | — | — | 16 | 6 | 6 | — | — | — | — |
| Octanoic acid | — | — | 4 | 4 | 4 | — | 5 | — | — |
| Water | 10 | 10 | — | — | — | 10 | 5 | — | — |

TABLE 3

Results of the microbiological tests against bacteria

| | [AWK] | *Staphylococcus aureus* ATCC 6538 (K 3212) Inoculum $7.05 \times 10^8$ CFU/ml | | *Escherichia coli* ATCC 10536 (K 2124) Inoculum $1.07 \times 10^9$ CFU/ml | |
|---|---|---|---|---|---|
| Product | % | 1 Min. RF | 5 Mins. RF | 1 Min. RF | 5 Mins. RF |
| Comparison formulation 1 | 0.1 | 1.3 | >4.87 | >5.2 | >5.3 |
| | 0.3 | 3.4 | >4.87 | >5.2 | >5.3 |
| Comparison formulation 2 | 0.1 | 0.04 | >4.87 | 3.69 | >5.3 |
| | 0.3 | 0.59 | >4.87 | >5.2 | >5.3 |
| Formulation 1 | 0.1 | 3.42 | >4.87 | >5.2 | >5.3 |
| | 0.3 | >4.9 | >4.87 | >5.2 | >5.3 |
| Formulation 2 | 0.1 | 0 | 0.09 | 1.17 | >5.3 |
| | 0.3 | 0.03 | >4.87 | >5.2 | >5.3 |
| Formulation 3 | 0.1 | >4.9 | >4.87 | >5.2 | >5.3 |
| | 0.3 | >4.9 | >4.87 | >5.2 | >5.3 |
| Formulation 4 | 0.1 | 3.04 | >4.87 | >5.2 | >5.3 |
| | 0.3 | >4.9 | >4.87 | >5.2 | >5.3 |
| Formulation 5 | 0.1 | 3.2 | >4.87 | >5.2 | >5.3 |
| | 0.3 | >4.9 | >4.87 | >5.2 | >5.3 |

AWK = concentration used; RF values = germ reduction in LOG stages

TABLE 4

Results of the DVG fungicidal activity test

| | [AWK] | *Saccharomyces cerevisiae* ATCC 9763 (K 5011) Inoculum $1.36 \times 10^7$ CFU/ml | | *Aspergillus niger* ATCC 16404 (K7444) Inoculum $1.07 \times 10^9$ CFU/ml | |
|---|---|---|---|---|---|
| Product | % | 5 Mins. RF | 30 Mins. RF | 5 Mins. RF | 30 Mins. RF |
| Comparison formulation 1 | 0.3 | 0.53 | 0.55 | 0 | 0 |
| | 1.0 | 0.71 | 1.4 | 0 | 0 |
| Comparison formulation 2 | 0.3 | 0.21 | 0.24 | 0 | 0 |
| | 1.0 | 0.24 | 1.1 | 0 | 0 |
| Formulation 1 | 0.3 | 2.88 | >3.19 | 0 | 0 |
| | 1.0 | >3.18 | >3.19 | 0 | 0.02 |
| Formulation 2 | 0.3 | 0.55 | >3.19 | 0 | 0.38 |
| | 1.0 | >3.18 | >3.19 | 0.22 | 0.85 |

TABLE 4-continued

Results of the DVG fungicidal activity test

| Product | [AWK] % | Saccharomyces cerevisiae ATCC 9763 (K 5011) Inoculum 1.36 × 10⁷ CFU/ml | | Aspergillus niger ATCC 16404 (K7444) Inoculum 1.07 × 10⁹ CFU/ml | |
|---|---|---|---|---|---|
| | | 5 Mins. RF | 30 Mins. RF | 5 Mins. RF | 30 Mins. RF |
| Formulation 3 | 0.3 | >3.18 | >3.19 | 0.31 | 0.54 |
| | 1.0 | >3.18 | >3.19 | 1.56 | 4.02 |
| Formulation 4 | 0.3 | 3.18 | 3.19 | 0.39 | 0.87 |
| | 1.0 | 3.18 | 3.19 | 1.34 | >4.02 |
| Formulation 5 | 0.3 | 3.18 | 3.19 | 0.61 | 1.3 |
| | 1.0 | 3.18 | 3.19 | 1.74 | >4.02 |
| Formulation 6 | 0.3 | 2.89 | — | — | — |
| | 1.0 | >3.18 | — | 0.06 | 0.06 |
| Formulation 7 | 0.3 | >3.18 | — | — | — |
| | 1.0 | >3.18 | — | 0.06 | >4.02 |

AWK = concentration used; RF values = germ reduction in LOG stages

It is clear from the results that the fungicidal activity of the peracid ester can be significantly improved by the addition of hydrogen peroxide and reduction of the peracid ester content.

What is claimed is:

1. A method of disinfecting washing textiles comprising a step of washing textiles in a disinfecting component, the disinfecting component comprising a combination of peracids and at least one fatty acid for reducing the fiber-damaging effect of the peracid.

2. The method claimed in claim 1, wherein the disinfecting component comprises between 1 and 20% by weight of peracid in combination with 0.1 to 10% by weight of fatty acid, the balance to 100% by weight water and/or other active substances or auxiliaries.

3. The method claimed in claim 1, wherein the disinfecting component additionally comprises
   a) at least one hydrotrope and/or
   b) at least one surfactant component and/or
   c) at least one complexing component.

4. The method claimed in claim 1 wherein the step of washing comprises washing textiles which are sensitive to oxidative disinfectants and/or heat at a temperature of 10 to 55° C.

5. The method claimed in claim 4, wherein the textiles which are sensitive to oxidative disinfectants and/or temperature contain materials selected from wool, silk, viscose, polyacrylics, polyamide, acetate and lyocell.

6. The method claimed in claim 1, wherein the disinfecting component is used together with standard speciality, color, fully-built and light-duty detergents.

7. The method claimed in claim 1, wherein the disinfecting component contains as peracid an organic compound selected from
   a) the peracids or salts of peracids corresponding to general formula I:

in which R² is hydrogen or an alkyl group containing 1 to 4 carbon atoms and x is a number from 1 to 4, and br
   b) phthalimidopercarboxylic acids (II) where the percarboxylic acid contains 1 to 18 carbon atoms, and/or
   c) compounds corresponding to formula III:

in which R¹ is an alkyl or alkenyl group containing 1 to 18 carbon atoms.

8. The method claimed in claim 7, wherein
   a) peracids in which R² is hydrogen or a methyl group are present as the peracids of general formula I and/or
   b) pthalimidoperacids in which in the percarboxylic acid contains 1 to 8 carbon atoms are present as the peracids and/or
   c) peracids with an alkyl or alkenyl group containing 1 to 12 carbon atoms are present as the peracids of general formula III.

9. The method claimed in claim 7, wherein one or more compounds selected from peracetic acid, perpropionic acid, peroctanoic acid, phthalimidoperhexanoic acid, phthalimidoperoctanoic acid, persuccinic acid, persuccinic acid monomethyl ester, pergiutaric acid, pergiutaric acid monomethyl ester, peradipic acid, peradipic acid monomethyl ester, persuccinic acid, persuccinic acid monomethyl ester are present as the peracids.

10. The method claimed in claim 1 wherein an aqueous disinfecting washing solution containing 0.001 to 2% by weight of peracid, based on the disinfecting washing solution as a whole, is produced by addition of the disinfecting component.

11. The method claimed in claim 1, wherein an aqueous disinfecting washing solution which additionally contains 0.005 to 2% by weight of hydrogen peroxide, based on the disinfecting washing solution as a whole, is produced by addition of the disinfecting component.

12. The method claimed in claim 1, wherein fatty acids containing 8 to 12 carbon atoms are present as the fatty acid.

13. The method claimed in claim 1, wherein the hydrotrope a) is selected from xylene, octyl, naphthyl and alkylbenzenesulfonates, the alkyl group in the last of these containing between 6 and 16 carbon atoms.

14. The method claimed in claim 1, wherein the surfactant component b) is selected from the groups of anionic, cationic, nonionic, amphoteric surfactants, protein hydrolyzates, alkylamine oxides, silicone compounds and phosphoric acids esters and salts thereof.

15. The method claimed in claim 14, wherein the surfactant component b) is a cationized protein hydrolyzate.

16. The method claimed in claim 1, wherein the step of washing comprises introducing the disinfecting component into the disinfecting washing process as an aqueous solution, gel, emulsion, paste, dispersion, powder, granules, flakes, pearls, tablet, block or extrudate.

17. The method claimed in claim 1, further comprising a step of diluting the disinfecting component with water before or during the step of washing.

18. The method claimed in claim 17, wherein the dilution factor is between 10 and 10,000.

19. The method claimed in claim 1, wherein the disinfecting component contains an ester peracid as the peracid and more than 35% by weight of hydrogen peroxide, based on the composition as a whole, is additionally present.

20. The method claimed in claim 1, wherein the disinfecting component contains a peracid and octanoic acid and, in addition, octyl sulfonate and/or a cationized protein hydrolyzate.

21. A method of reducing textile fiber-damage from disinfecting washing textiles with a peracid comprising a step of washing said textiles in a disinfecting component, the disinfecting component comprising a combination of peracids and at least one fatty acid for reducing the fiber-damaging effect of the peracid.

* * * * *